(12) United States Patent
Bublitz (10) Patent No.: US 11,064,879 B2
(45) Date of Patent: Jul. 20, 2021

(54) HOLOSCOPIC, OPTICAL COHERENCE TOMOGRAPHY

(71) Applicant: Carl Zeiss Meditec AG, Jena (DE)

(72) Inventor: Daniel Bublitz, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 194 days.

(21) Appl. No.: 16/440,966

(22) Filed: Jun. 13, 2019

(65) Prior Publication Data

US 2019/0380573 A1    Dec. 19, 2019

(30) Foreign Application Priority Data

Jun. 13, 2018 (DE) .......................... 102018114108.4
Nov. 29, 2018 (DE) .......................... 102018130396.3

(51) Int. Cl.
*A61B 3/10* (2006.01)

(52) U.S. Cl.
CPC .................. *A61B 3/102* (2013.01)

(58) Field of Classification Search
CPC .................................................... A61B 3/102
USPC ....................................................... 351/206
See application file for complete search history.

(56) References Cited

U.S. PATENT DOCUMENTS

| 10,568,503 B2 * | 2/2020 | Bublitz .................. A61B 3/102 |
| 2014/0028974 A1 | 1/2014 | Tumlinson |
| 2017/0224208 A1 | 8/2017 | Bublitz et al. |
| 2018/0020912 A1 | 1/2018 | Bublitz et al. |
| 2019/0056214 A1 * | 2/2019 | Everett ............. G01B 9/02028 |

FOREIGN PATENT DOCUMENTS

| DE | 102014115153 A1 | 4/2016 |
| DE | 102014115155 A1 | 4/2016 |
| DE | 102014115157 A1 | 4/2016 |

(Continued)

OTHER PUBLICATIONS

Hillmann et al., "Efficient holoscopy image reconstruction," *Optics Express*, vol. 20, No. 19, Sep. 10, 2012 (17 pgs).

(Continued)

*Primary Examiner* — Mohammed A Hasan
(74) *Attorney, Agent, or Firm* — Patterson Thuente Pedersen, P.A.

(57) ABSTRACT

A method for holoscopic, optical coherence tomography for an object, wherein the method includes providing source radiation and splitting the source radiation into illumination radiation and reference radiation, illuminating an illumination field on the object with illumination radiation, said illumination field having an areal extent transverse to the direction of incidence, collecting illumination radiation scattered back from the object as measurement radiation, separating the measurement radiation collected from the object from the illumination radiation, and overlaying the measurement radiation with reference radiation and detecting an interference signal of the overlaid radiations with at least one areal detector with a two-dimensional extent, wherein the object in the illumination field is simultaneously illuminated by more than one spatial radiation mode, wherein the radiation modes of the illumination in the illumination field are spatially and temporally coherent with one another but have a fixed phase difference from one another.

19 Claims, 6 Drawing Sheets

(56) References Cited

FOREIGN PATENT DOCUMENTS

DE      102015101251  A1    7/2016
WO    WO 2017/137567  A1   8/2017

OTHER PUBLICATIONS

Kumar et al., "Subaperature correlation based digital adaptive optics for full field optical coherence tomography," *Optics Express*, vol. 21, No. 9, May 6, 2013 (17 pgs).

* cited by examiner

HOLOSCOPIC, OPTICAL COHERENCE TOMOGRAPHY

RELATED APPLICATION

The present application claims priority to German Application No. 102018114108.4, filed Jun. 13, 2018, and German Application No. 102018130396.3, filed Nov. 29, 2018, which are hereby each incorporated herein in their entirety by reference.

TECHNICAL FIELD

The invention relates to a method for holoscopic, optical coherence tomography for an object, in particular for an eye. In particular, the method includes providing source radiation and splitting the source radiation into illumination radiation and reference radiation, illuminating an illumination field on the object with illumination radiation, said illumination field having an areal extent transverse to the direction of incidence, collecting illumination radiation scattered back from the object as measurement radiation, separating the measurement radiation collected from the object from the illumination radiation guided to the object, and overlaying the measurement radiation with reference radiation and detecting an interference signal of the overlaid radiations with at least one areal detector with a two-dimensional extent.

The invention further relates to an optical coherence tomography device for examining an object, in particular an eye, by means of holoscopy, said optical coherence tomography device including an illumination device for providing source radiation, an illumination and measurement beam path, which comprises a splitting element for splitting the source radiation into illumination radiation and reference radiation, illuminates an illumination field in the object with the illumination radiation, said illumination field having an areal extent transverse to the direction of incidence, and collects illumination radiation scattered back from the object as measurement radiation, a reference beam path which provides an optical path length for the reference radiation, said optical path length equaling an optical path length from the splitting element to the illumination field and back to an overlay site, a detection beam path which receives the measurement radiation from the illumination and measurement beam path and the reference radiation from the reference beam path, and overlays said measurement radiation and reference radiation at the overlay site and guides these to an areal detector with a two-dimensional extent.

BACKGROUND

Methods and coherence tomography devices are known from DE 102014115157 A1. Similar approaches are also found in DE 102014115153, DE 102014115155 A1, DE 102015101251 A1 and WO 2017/137567 A1. In ophthalmology, optical coherence tomography (OCT) is an established method for imaging the eye. It allows three-dimensional imaging, which is very helpful in the diagnosis of eye disease and the course thereof In particular, diseases of the retina should be specified in this context, such as glaucoma or age-related macular degeneration. The lateral resolution (x and y) in OCT systems is set by the numerical aperture of the employed optics. By contrast, the axial resolution is calculated from an interference pattern and, as a rule, is very much greater than the depth of field of the imaging; the latter, in turns, depends on the numerical aperture, more precisely being proportional to $1/NA^2$. In Fourier domain OCT, which uses a broadband or wavelength-adjustable radiation source and which is usually employed, the depth resolution is inversely proportional to the spectral bandwidth, more precisely proportional to $\lambda^2/\Delta\lambda$, where $\lambda$ is the mean wavelength and $\Delta\lambda$ is the bandwidth.

Both a high lateral resolution and a high axial resolution are required for measuring objects, such as the retina of the human eye, for example. At the same time, the capturable and hence illuminated volume should be as large as possible in its depth (along the optical axis); this requires a small numerical aperture of the optical system. The lateral resolution requires a large numerical aperture. Hence, the extent of the depth-accessible range and the lateral resolution are ultimately linked to one another in the prior art via the numerical aperture of the optical system and cannot be set independently of one another.

US 2014/0028974 A1 has disclosed an imaging method which builds on OCT. Here, a line is projected onto an object by an imaging system. The back-scattered radiation is combined with reference radiation in interfering fashion and guided to a detector, with a confocal filtering being undertaken in one direction. To this end, an astigmatic optical unit is used. The depth resolution is implemented by means of optical coherence tomography. In the case of a spectroscopic analysis of the radiation, use is made of a two-dimensional detector whose one extent serves for confocal filtering in respect of the line-shaped illuminated region and whose other extent resolves the spectral information. Lateral resolution and accessible depth range are also linked in the approach according to US 2014/0028974 A1.

In the case of a scanning OCT system, the diameter of the pupil accessible on the eye is usually between 1 mm and 1.5 mm. This yields a lateral resolution of approximately 15 µm and a depth-capturable region of 3 mm extent. A better lateral resolution would be achieved with a higher numerical aperture of the optical system. However, this would reduce the depth-capturable region at the same time. Moreover, aberrations increase with numerical aperture. In the case of known OCT systems, which use up to 1.5 mm diameter in the pupil of the eye, it is possible to usually neglect the defocusing as a higher-order aberration; however, astigmatism and coma increase for larger pupils. Therefore, it is not possible to achieve a diffraction-limited resolution.

SUMMARY

A high lateral resolution is desired for certain applications, in particular for diagnosing age-related macular degeneration. A lateral resolution of approximately 5 µm is required to identify the early stages of this disease. However, a scannable depth measuring range of approximately 3 mm is required since the assumption is made that the age-related macular degeneration is accompanied by a blood vessel formation in deeper tissue layers. Moreover, a good signal-to-noise ratio is required to detect such vessels. Therefore, the generic DE 102014115157 A1 provides a solution that improves the lateral resolution when measuring on the retina of the human eye in holoscopic, optical coherence tomography, without restricting the accessible depth range.

OCT systems that employ a spatially resolved detector array and coherent evaluation algorithms, which are known from digital holography, are referred to as holoscopic, optical coherence tomography devices in the literature.

Here, the term "holoscopic system" relates in general to an interferometric OCT system with more than one lateral sensor element. In this notation, holoscopic wide-field systems, line-scanning OCT systems, and small field scanning OCT systems, for example, are holoscopic systems, while confocal systems are not, even if they use a balanced detection with two sensors.

In such holoscopic multichannel systems, the optical unit is designed in such a way that light is imaged on the detector elements in diffraction-limited fashion such that each detector element is able to detect only a very restricted etendue.

The illumination in confocal systems is implemented using a spatially coherent single-mode source. Fiber-coupled illumination systems are usually used. The light leaving this single-mode illumination fiber has a TEM00 mode spectrum with an etendue of approximately $2*\pi*\lambda^2$. The etendue of the detectable light scattered back by the sample is identical to the illumination etendue and the mode form. For this reason, the part of a lightwave field carrying the etendue of a TEM00 mode is generally referred to as a spatial mode below.

Therefore, confocal systems with only one lateral sensor element thus are single-mode in terms of detection, while systems with more than one spatial sensor element are multi-mode in terms of detection. Consequently, the number of detector elements (pixels) is a measure for the number of detection modes.

OCT systems can be illuminated in spatially coherent or incoherent fashion. Preferably, "time domain" systems are illuminated at least in part using incoherent lightwave fields such as LEDs or thermal lamps. However, the measured values cannot be reconstructed coherently in such systems. By way of example, white-light interferometers are often realized in this manner.

By contrast, the usual OCT systems (e.g., confocal systems, full-field holoscopic systems, line-scanning systems and small field scanning systems) are illuminated by a spatially fully coherent, spatially single-mode source in order to facilitate a coherent reconstruction.

In all systems where the illumination is implemented by a spatial mode while the detection is implemented in multi-mode fashion, it is possible to match the field distributions of the illumination and detection in a reference plane (e.g., the focal plane) by an appropriate design of the optical unit. Then, only the parts of the sample that can also be detected are illuminated. However, the illumination mode and the detection modes run apart outside of the focal plane on account of the different etendues. Therefore, a certain "mode mismatch" outside of the focus is unavoidable in such systems.

The basic idea of the "multi-direction scanning OCT" (WO 2017/137567 A1) lies in illuminating a sample point with a spatial single mode and detecting the latter using a matched detection mode with an associated sensor element. Then, this combined illumination/detection mode can be switched over in time-sequential fashion between various illumination directions. If the data measured from the sample from different directions in this way are coherently reconstructed, it is possible to capture a higher etendue in comparison with a confocal system and hence possible to capture a higher lateral resolution with a sufficient focal depth (that of the individual mode).

As a rule, commercial OCT systems used on the eye are currently confocal systems. In these systems, there is a fixed relationship between the pupil size, the lateral resolution and the achievable depth range (Rayleigh length). Doubling the pupil size facilitates a double lateral resolution, but only a depth range restricted by a factor of 4. For this reason, all systems used for retina imaging have a similar pupil size and hence similar lateral resolutions in the region of approximately 17 µm.

A possible way to break this limitation lies in using a plurality of sensors in any technical arrangement (e.g., wide-field, line scanning or small field scanning). However, for as long as these systems are illuminated using only a single illumination mode, as is the case in all systems known from the prior art, it is not possible to circumvent the just described "mode mismatch", which greatly limits the effectively achievable depth range by the vignetting effect accompanying it.

Time-sequential systems such as multi-direction scanning OCT require longer recording times. All movement artifacts in the case of measurements on living eyes, for example, change the phase information items of the individual measurements and consequently make a coherent reconstruction more difficult.

The invention is based on the object of extending the accessible depth range in holoscopic, optical coherence tomography.

The invention is defined in claims 1 and 7. Advantageous developments are the subject matter of the dependent claims.

The discovery underlying the invention, which can be ascribed to the inventor for the first time, consists of spatial coherence, as a necessary property for a coherent reconstruction in holoscopic coherence tomography, and a multi-mode illumination wave field not precluding but instead advantageously complementing one another.

Therefore, provision is made of a method for holoscopic, optical coherence tomography of an object, in particular an eye, in which source radiation is provided and split into illumination radiation and reference radiation. An illumination field on the object, which has an areal extent transverse to the direction of incidence, is illuminated by the illumination radiation. Illumination radiation scattered back at the object is collected as measurement radiation. It is separated in the beam path from the illumination radiation guided to the object and overlaid with the reference radiation. A detector detects the overlaid radiations and hence detects an interference signal. The latter is evaluated in a manner known per se using coherent evaluation algorithms. The detector can undertake a balanced detection. A spatially non-resolving, confocal detector in combination with a scanner for scanning the object come into question as a detector. Further, the detector can have spatial resolution in one or two dimensions, e.g., be an areal detector with a two-dimensional extent, wherein the individual detector elements may also be spaced apart from one another.

On account of the aforementioned discovery, the object in the illumination field is illuminated simultaneously by more than one spatial radiation mode. The different radiation modes of the illumination are spatially and temporally coherent to one another in the illumination field. However, they have a fixed phase difference from one another; i.e., they differ by different static initial phases.

An illumination device that provides source radiation is provided in respect of the optical coherence tomography device for the optical and holoscopic examination of an object. An illumination and measurement beam path comprises its splitting element for splitting the source radiation into illumination radiation and reference radiation. Further, it illuminates an illumination field on the object with an areal extent transverse to the direction of incidence with the illumination radiation and collects illumination radiation scattered back from the object as measurement radiation. A detection beam path receives the measurement radiation from the illumination and measurement beam path and the reference radiation from a reference beam path and overlays these at an overlay site. It guides the latter onto a detector, e.g., a confocal detector or a two-dimensionally extended areal detector.

Further, the illumination and measurement beam path illuminates the object in the illumination field simultaneously by more than one spatial radiation mode. The radiation modes of the illumination are temporally and spatially coherent to one another in the illumination field but have a fixed phase difference from one another. The fixed phase difference is produced by virtue of the illumination modes having unequal static initial phases in the production thereof.

In a preferred configuration of the method and coherence tomography device, the initial phases or phase differences have a statistical or quasi-random distribution over the illumination field.

By way of example, this can be achieved from a technical point of view by virtue of spatially completely coherent light of a spatial single-mode source (such as SLD or swept source laser) illuminating a static phase plate, e.g., a lithographic diffusing plate. The light transmitted through this element has a significantly larger etendue but is not influenced in temporal and spatial coherence because it is static and only introduces small travel time differences. The element is designed and arranged in such a way that the etendue is increased by a certain factor, which is referred to as illumination mode number.

A technically equivalent description is to use a single-mode source with an $M^2$ (beam parameter product) of approximately 1 and transform the beam with the phase element in such a way that an $M^2$ of significantly over 1 is produced.

Here, the etendue is measured in each contiguously illuminated sample zone in order to delimit the novel method from multi-spot systems, in which a plurality of confocal sensors simultaneously measure mutually separated regions of the sample and in which an $M^2$ of approximately 1 can be measured per spot, but also, overall, a significantly larger overall etendue. The essential feature of the novel arrangement consists of the different illumination modes overlaying in the sample volume and hence being able to simultaneously interact with a plurality of detector channels. This can also be identified by virtue of the fact that the intensity of the illumination wave is modulated in the field plane and consequently deviates from typical Gaussian beam profiles.

Therefore, provision is made in a development of method and coherence tomography device for the areal detector to comprise detector elements lying next to one another in an image plane, between which there may also be gaps. Each detector element corresponds to a detector mode. The number of detector elements and the number of illumination modes are matched to one another, preferably with a bijective association.

Nevertheless, information reconstruction can be carried out if use is made of a number of detector elements or detector modes that is less than the number of illumination modes. To this end, spatial frequencies that are transmitted by mode interaction from the illumination to the detection are evaluated. To this end, the coherence tomography device comprises a control unit which carries out the information reconstruction and which preferably also undertakes the coherent evaluation using the holoscopic coherence tomography principle.

The invention is based on the discovery that the spatial coherence, as a necessary property for coherent reconstruction in holoscopic coherence tomography, and a multi-mode illumination wave field do not preclude one another but instead are able to advantageously complement one another. Embodiments therefore provide for the illumination field to contain more than one spatial radiation mode in the holoscopic, optical coherence tomography. Thus, the illumination is implemented in multi-modal fashion. The different radiation modes are spatially and temporally coherent to one another in the illumination field. They have a fixed phase difference from one another; i.e., they differ by different static initial phases. Occasionally, speckles occur in such an illumination field. The effect of these speckles is removed again in embodiments by incoherent averaging. To this end, a plurality of recordings are made, which are displaced in relation to one another by at least one illumination speckle grain. In this way, the recordings become independent of one another from the mathematical point of view and the speckle structure disappears on account of the averaging. Alternative embodiments likewise make a plurality of recordings, which are displaced in relation to one another by at least one illumination speckle grain. They compensate the speckle effect by virtue of setting up a system of equations and suppressing multiply scattered signal components by way of a linear regression of these equations. This increases the image contrast.

In a particularly simple embodiment in view of speckle suppression, the illumination and measurement beam path produces a speckle pattern in the illumination field, which comprises no axis of symmetry.

For the purposes of producing the illumination modes, the illumination and measurement beam path may have a diffusing element that is positioned in a field plane of the beam path.

It goes without saying that the aforementioned features and those yet to be explained below can be used not only in the combinations specified but also in other combinations or on their own, without departing from the scope of the present invention.

The above summary is not intended to describe each illustrated embodiment or every implementation of the subject matter hereof. The figures and the detailed description that follow more particularly exemplify various embodiments.

BRIEF DESCRIPTION OF THE DRAWINGS

The invention will be explained in more detail below on the basis of exemplary embodiments, with reference being made to the attached drawings, which likewise disclose features essential to the invention. These exemplary embodiments serve merely for elucidation and should not be interpreted as restrictive. By way of example, a description of an exemplary embodiment with a multiplicity of elements or components should not be interpreted to the effect that all these elements or components are necessary for implementation purposes. Rather, other exemplary embodiments also may contain alternative elements and components, fewer elements or components or additional elements or components. Elements or components of different exemplary embodiments can be combined with one another, unless indicated otherwise. Modifications and developments which are described for one of the exemplary embodiments may also be applicable to other exemplary embodiments. In order to avoid repetition, the same elements or corresponding elements in the various figures are denoted by the same reference signs and are not explained a number of times. In the figures.

The exemplary embodiments below relate to holoscopic coherence tomography on the eye. However, they can also be used on other objects; the reference to the eye is purely exemplary.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The human eye is an optical system that simultaneously comprises both the retina, and hence a certain field, and the pupil, and consequently the far-field distribution. The mathematical pupil whose field distribution corresponds to the Fourier transform of the retinal field distribution lies only a few millimeters in front of the eye.

Figure 1A:
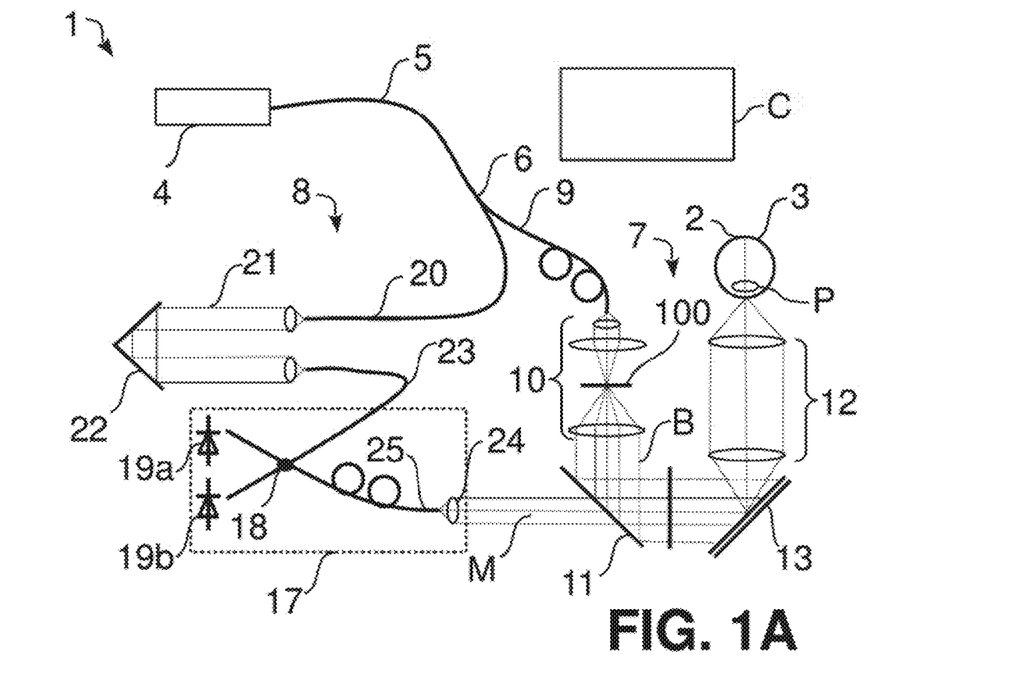
FIG. 1A shows a schematic illustration of a holoscopic optical coherence tomography (OCT) device with scanning, confocal imaging of an eye.
Figure 1B:
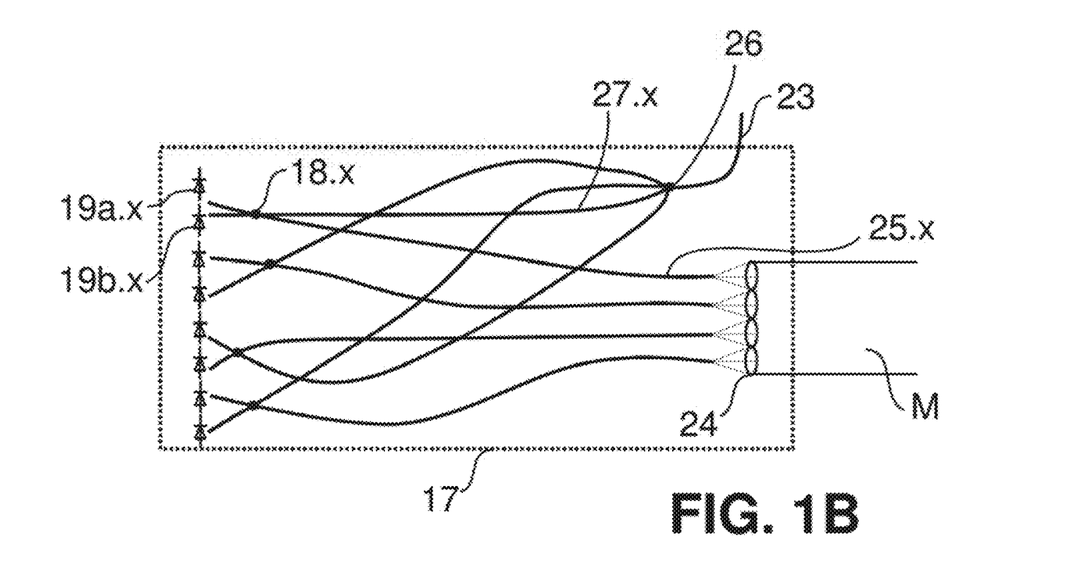
FIG. 1B shows a schematic illustration of a detector device for an OCT with modified imaging in relation to FIG. 1A.
Figure 1C:
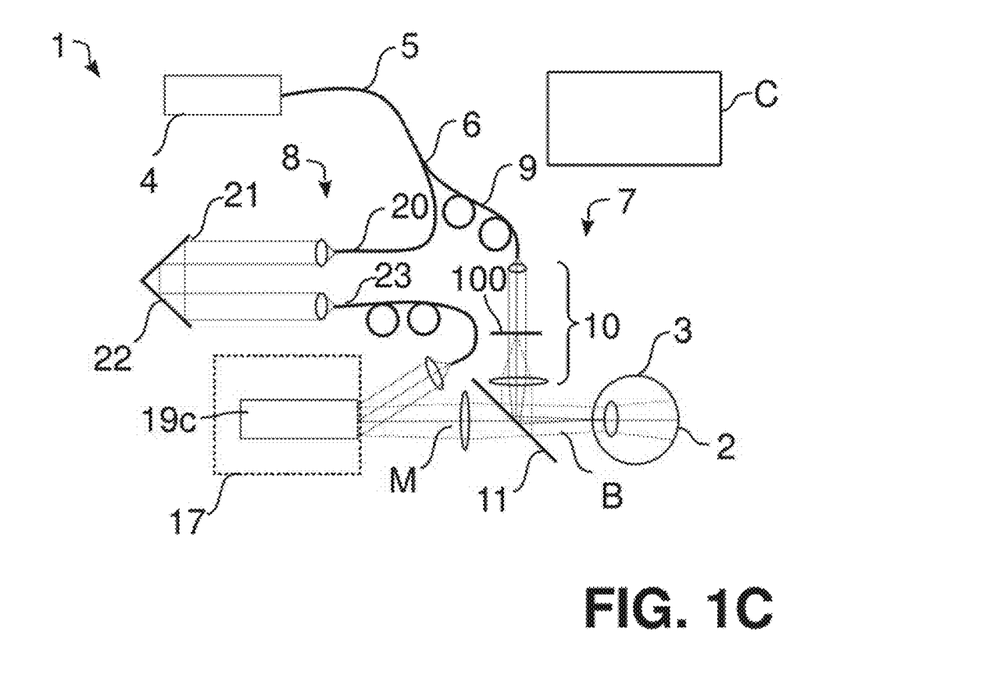
FIG. 1C shows a schematic illustration of the holoscopic optical OCT with imaging of the eye on an areal detector.

FIGS. 1A and 1C each show an OCT 1, which records three-dimensional images, inter alia of a retina 2 of an eye 3. FIG. 1B shows a modified detector device for the OCT 1 of FIG. 1A. The described embodiments are always described using the example of a fiber-based swept source system; however, they can likewise be transferred to free beam designs and/or time domain systems and frequency domain systems.

Source radiation of a radiation source 4 that is tunable in terms of its wavelength, for example of a corresponding laser, is coupled into a fiber 5. By way of example, the source radiation lies in the infrared wavelength range. This wavelength range is also denoted "light" in the following description. This term should comprise all radiation of the electromagnetic spectrum that satisfies the laws of optics. In the design of FIGS. 1A and 1B, the OCT 1 carries out scanning confocal imaging; imaging is implemented on an areal detector in the design of FIG. 1C.

In all fiber-based designs, the fiber 5 merges into a splitter 6, which divides the source radiation among a measurement arm 7 and a reference arm 8. In the measurement arm 7, the splitter 6 is adjoined by a fiber 9 and the illumination radiation B emerging at the end of the fiber is modified in respect of the illumination modes by means of an illumination optical unit 10 and then guided to a beam splitter 11. From there, it reaches a front optical unit 12, which focuses the illumination radiation B at a focus lying in the eye 3. In the design of FIGS. 1A and 1B and, optionally, in the embodiment of FIG. 1C as well, a scanner 13, which deflects the focus onto the retina 2 along two axes perpendicular to the direction of incidence, i.e., laterally, is situated between the beam splitter 11 and the front optical unit 12. Below, the coordinates of this deflection are denoted by x and y. The z-position of the focus can be set by adjusting the front optical unit 12.

The illumination radiation in the illumination focus on the retina 2 is scattered back from different depths z within the depth-of-field range.

The back-scattered radiation is collected by the front optical unit 12 as measurement radiation M and (to the extent this is present) guided to the scanner 13. Here, it is descanned, and so the measurement radiation M is present as a beam at rest after the scanner 13.

The beam splitter 11 separates the measurement radiation M from the illumination radiation B and guides the former to a detector device 17. In the embodiment of FIG. 1A, the detector device 17 comprises a beam splitter/unifier 18 and two sensors 19a and 19b. Confocal imaging is undertaken. The design of FIG. 1A realizes a "balanced detection", as is known in the art. In FIG. 1B, a multiplicity of balanced sensor pairs 19a/19b are provided in order to carry out a multi-modal detection. In FIG. 1C, the latter is implemented in the far field and an areal sensor 19c has a spatial resolution, i.e., it allows a resolution of the intensity distribution over the beam cross section. The detector device 17 preferably lies in a pupil plane 30 of the measurement beam path, i.e., in a plane that is conjugate to the plane of the pupil P of the eye 3, through which the measurement radiation M emerges. However, since the lightwave field, if known in a plane with absolute value and phase, can be calculated for any other plane, the detection may also be implemented in other planes, e.g., conjugated to the retina as in FIG. 1C.

Reference radiation R from the reference arm 8 is also coupled into the detector device 17 from a fiber 23 (FIGS. 1A and B) or by oblique incoming radiation on the areal detector (FIG. 1C). The latter has a fiber 20 after the splitter 6.

In the embodiments shown in FIGS. 1A and 1C, the reference arm 8 has a path length adaptation device 21, which serves to set the length of the reference arm 8 to fit to the position of the retina 2 of the eye 3. To this end, the radiation is coupled out of the fiber 20 and then guided via a retroreflector 22, the position of which can be adapted. Then, the reference radiation R is overlaid with the measurement radiation M and guided to the sensors 19a and 19b or the areal detector 19c.

The path length adaptation device 21 is embodied as a free beam path. This is likewise optional, just like the use of a retroreflector 22. The prior art has disclosed various measures for adjusting the optical path length of a beam.

The detector device 17 is embodied as a so-called "balanced detection" in FIGS. 1A and B. This, too, is optional. The balanced detection is advantageous in that a common mode component in the superposition of reference radiation R and measurement radiation M can be suppressed in a particularly simple manner. Alternatively, such a suppression could be dispensed with if use were to be made of a single detector only, for example the sensor 19b, and the beam splitter/unifier 18 were to be embodied as a pure beam unifier.

The interference between reference radiation R and measurement radiation M is transformed to produce an image, as is known for scanning holoscopic optical coherence tomography. Since the wavelength of the source radiation is tuned, the Fourier domain principle is applied when producing the image; this is known from the prior art as a matter of principle.

Only a single mode of the detection is evaluated in the design of FIG. 1A; accordingly, the measurement radiation M is collected by way of a single lens 24 in a plane conjugated to the plane of the retina 2 and made to interfere with reference radiation from the optical fiber 23 at the beam splitter/unifier 18 by means of an optical fiber 25 and guided onto the sensor pair 19a/19b. By contrast, a multi-modal confocal detection is carried out in the design of FIG. 1B by virtue of the measurement radiation M being coupled into multiplicity of optical fibers 25.x from a plane conjugate to the pupil plane by means of a lens 24 embodied as a mini-lens array. Four optical fibers are shown in exemplary fashion and one of them is denoted by the reference sign 25.x. If use is made of n optical fibers with a corresponding number of mini-lenses in the mini-lens array 24, the radiation in the optical fiber 23, i.e., the reference radiation, is also split using a beam splitter 26 into total of n optical fibers, of which the optical fiber 27.x is denoted in exemplary fashion. The optical fibers 25.x and the optical fibers 23.x are linked in pairs at beam splitters/unifiers 18.x, and so the radiation reaches sensor pairs 19a.x/19b.x. This procedure is carried out accordingly for all optical fibers 25.x, the measurement radiation M from the mini-lens array 24 and the reference radiation R from the optical fiber 27.x. Overall, each mini-lens of the mini-lens array 24 represents a detection channel, which corresponds to a detector element. Each sensor pair 19.a.x/19.b.x corresponds to a detector element in the detector device 17.

For the purposes of carrying out the image generation, the OCT 1 has a controller C, which receives a signal about the wavelength tuning and the measurement signals of the detector device 17. Optionally, the controller C actuates the radiation source 4 for wavelength tuning; therefore, it knows the currently prevalent wavelength in the system and hence can accordingly assign the measurement signals. The sensors receive measurement radiation M from an object field on the eye 3. In the embodiment according to FIG. 1A or B, the sensors 19A/19b or 19a.x/19b.x scan the intensity distribution in a spatially resolved manner together with the scanner. In the design of FIG. 1C, this is adopted by the areal detector 19c. If it optionally lies in an image plane, i.e., in a plane which, taking account of the imaging carried out by the front optical unit 12, the detector optical unit 14 and the further interposed optical elements, is conjugate to the plane of the retina 2, the individual pixels already contain the spatial information in the object field. By contrast, if it lies in the conjugate pupil plane 30, which is conjugate to the plane in which the pupil P of the eye 3 lies, the pixels capture the intensity distribution in the pupil plane, and hence the phase information items. This may also be used for image reconstruction, as is known. Naturally, a scanner 13 can also be used in the design of FIG. 1C for the purposes of capturing a larger object field.

In FIG. 1A or B, the beam splitter(s)/unifier(s) 18 and 18.x, respectively, combine(s) the measurement radiation M from the measurement arm 7 and the reference radiation R from the reference arm 8. As a result of the effect of the scanner 13, the sensors 19a/19b or 19a.x/19b.x capture the pattern of the interference between the measurement radiation M and the reference radiation R. The corresponding measures for producing such an interference, in particular the properties of the radiation source 4 and of the path length adaptation, required to this end, are known from the prior art for optical coherence tomography devices. An analogous statement applies to the design of FIG. 1C. The holoscopic evaluation is firstly explained in the patent documents cited at the outset and secondly also known from the publication Hillmann et al., "Efficient holoscopy image reconstruction", Optics Express, vol. 20, no. 19, 21247.

Illumination radiation with a single illumination mode would have such a small etendue that it would have a focus either in the vicinity of the retina 2 or in the vicinity of the anterior chamber. It is also possible to determine that the field distribution in the retinal plane and in the iris plane cannot be determined independently of one another in single-mode systems. For this reason, it would not be possible to record the entire eye 3 in holoscopic fashion, even if the coherence length would be sufficient.

What is therefore common to all variants is that provision is made of coherent multi-mode illumination, the illumination distribution and mode number of which is preferably adapted to the detection arrangement. Using this, it is possible to set the field size on the retina 2 and the detectable pupil size in the anterior chamber independently of one another (the possible optical resolution in the retina 2 however depends on the pupil size and the anterior chamber resolution depends on the retinal field size). As result, a real holoscopic whole-eye recording is possible.

The multi-modal illumination in the illumination radiation B is achieved by the illumination optical unit 10, which produces a field plane of the illumination in which a diffusing element 100 lies. By way of example, it brings about an illumination in an illumination field that lies in the eye 3, said illumination field having a speckle field distribution. Optionally, the diffusing element can be pivoted out in order to switch the microscope to conventional illumination.

Figure 2:
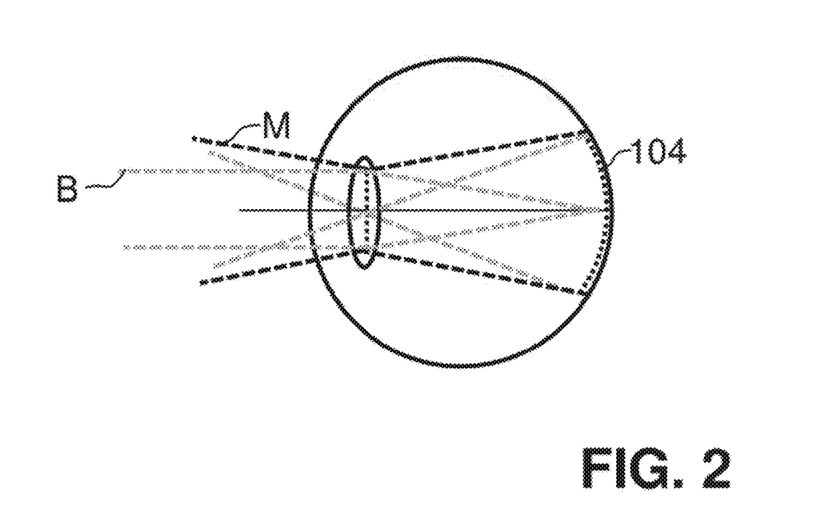
FIGS. 2 and 3 show the beam profiles in respect of an illumination in a conventional holoscopic system (FIG. 2) and in a system according to FIG. 1A, 1B or 1C (FIG. 3)
Figure 3:
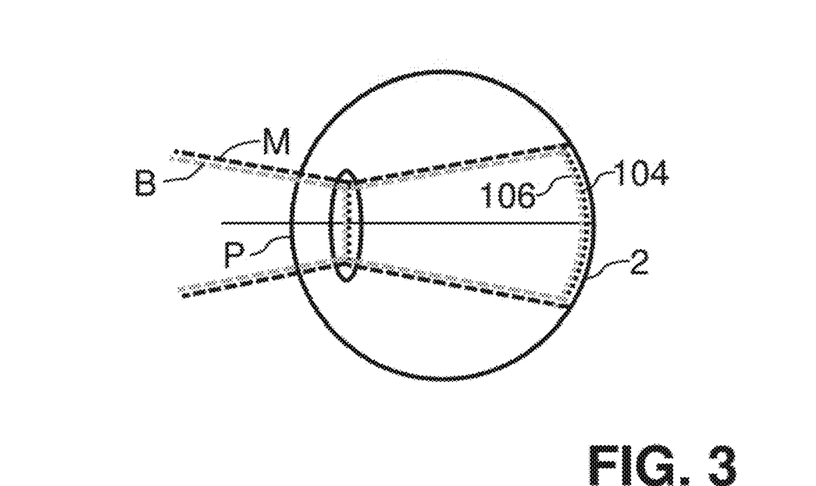

FIG. 2 shows the incidence of the illumination radiation B in the conventional single-mode case and the region covered by the measurement radiation M. It is clear that the illumination radiation B can only capture a small part of the measurement field 104.

By contrast, in the multi-modal illumination realized in FIGS. 1A to C, the measurement field 104 is exactly the same in terms of size as the illumination field 102. This applies both on the retina 2 and on the lens of the eye, and in the region of the pupil P.

From the view of the image evaluation, there are a number of preferred realizations. These proceed from the following deliberations:

If the retina 2 is illuminated by multi-mode speckle field distribution, this complex speckle-field function is multiplied by the complex back-scattering function of the retinal tissue and a "noisy" image of the retina is obtained. The images would also be noisy in conventional confocal images since a Gaussian beam distribution is multiplied by the complex back-scattering function of the retina in this case. If a sample is illuminated by an extended coherent multi-mode wave, this wave is modulated in its field strength in the form of speckles. The speckles have lateral dimensions that are determined by the numerical aperture of the illumination and that correspond to the size of the diffraction-limited resolution. In terms of depth, the speckles have axial extents that correspond to the wave-optical depth of field or Rayleigh length. Each of these excitation speckle grains has a random phase angle and a brightness that is described by the speckle statistics known per se to a person skilled in the art. If a plane illumination wave is assumed during the reconstruction of the data and the characteristics of the scattered illumination wave are not taken into account, the modulations of the illumination wave may become visible in the final image and disturb the image impression, especially in the case of small illumination apertures. Literature has disclosed that, for example, 3D retinal images recorded by holoscopic wide-field imaging have a significantly poorer contrast than images recorded by a confocal point scanner as a result of the significantly more efficient detection of multiple scattering. If holoscopic wide-field systems are combined with a partly confocal method, the multiple scattering can be significantly reduced; however, this also restricts the advantages of holoscopic imaging, such as the decoupling of lateral resolution and accessible depth range, for example.

Examples of such partly confocal systems known from the prior art comprise line scanners or "spinning disk" systems (with so-called Nipkow disks). The recording is implemented in confocal fashion in one direction in the case of line scanners, and so the accessible depth range and the lateral resolution can only be decoupled within the detection lines. In the case of Nipkow disks, the sample is scanned simultaneously by a plurality of confocal spots, and so the properties tend to correspond to a confocal system rather than a holoscopic detection system. The prior art, especially in microscopy, has various methods known by the term structured illumination. In contrast to partly confocal imaging, in which unwanted out-of-focus signals are suppressed in partly confocal fashion, it is a target of structured illumination to specifically measure the out-of-focus signal components and subtract these by calculation. To this end, the sample is illuminated by an intensity-modulated or structured lightwave. A plurality of recordings with different illumination patterns or pattern positions are realized from each sample point and the recordings are combined with one another by calculation during the evaluation.

Now, the multiply scattered sample light is suppressed in the image evaluation, without restricting the holoscopic advantages of decoupling the lateral resolution and accessible depth range. So that this is possible in the holoscopic imaging provided here, the illumination patterns must be structured at all depths of the sample.

In a first variant, the complex retinal back-scattering function is now additionally multiplied by the complex illumination field distribution with the multi-mode illumination used here, as a result of which there is a change in the speckle statistics. However, this effect has no impact on parameters such as lateral resolution and sensitivity. For this reason, it is a first option to consider the multi-mode illumination no further during the evaluation.

In a second variant, a plurality of complete holoscopic data records are recorded, in which the illumination speckle distribution in relation to the retina 2 is displaced in a random direction by more than one speckle grain, for example by random eye movements or by scanning the illumination distribution. The image data are evaluated in such a way that the image quality improves further, by virtue of the 3D displacement vectors between the holoscopic data records being estimated and corrected, and the recordings then being incoherently averaged. Hence, the lateral resolution of the images is maintained; however, the images have an improved sensitivity and are "despeckled". If the exact displacement vectors of the holoscopic partial data records are known or if these are estimated by cross correlations and if, moreover, the exact speckle function is known, the 3D reconstruction algorithms (with estimation and correction of the eye aberrations) known from holoscopy can be applied and the lateral resolution can consequently be doubled. Hence, a resolution of up to 2.5 μm in the lateral direction is achieved in the case of an eye pupil diameter of approximately 4.5 mm.

In a third variant, the sample is illuminated with a coherent scattered multi-mode lightwave field and the illumination speckles resulting in all planes of the sample are used for structured illumination. A plurality of 3D data records of a sample are recorded with scattered coherent illumination. No movement artifacts or optical aberrations are contained within the data records, or these were estimated and numerically corrected in advance, for example using algorithms that are otherwise known for holoscopic imaging. In this respect, reference is made to the publication Hillmann et al., "Efficient holoscopy image reconstruction", Optics Express, vol. 20, no. 19, 21247. The position of the illumination speckles in relation to a defined sample point is modified, for example by exploiting random sample movements (eye movement) or an active (e.g., motor-driven) adjustment, in such a way that the illumination speckles in the various recordings are displaced in relation to one another by at least one spectral grain. If n 3D data records of the sample are recorded in this manner, n measurement values $Y_i$, which were recorded with different but known illumination speckle brightnesses $X_i$, are obtained for each 3D data point. Hence, n equations of the following type:

$$Y_i = X_i * eS + mS$$

are set up. A total of n 3D data records are recorded. Here, i corresponds to the number of the data record and ranges from 1 to n, eS represents the signal that has been scattered once and mS represents the signal that has been scattered multiple times; these are complex variables. The illustrated equation can be set up independently for each sample point within the 3D cube. A linear regression over these equations with complex variables then supplies an image with the sought-after magnitude of the signal eS that has been scattered once. As a result of the random phase relationships, all speckles average out of the magnitude of the complex variables eS and mS. As a result of suppressing the multiply scattered signal mS, the image contrast is significantly better than in the case of holoscopic recordings and reaches the contrast range of confocal recordings. For various evaluations of the OCT data in the case of a coherent multi-mode illumination, it is necessary to be able to predict the exact functionality of the speckles at the various sample depths. A linear scattering model is assumed to this end. This means that the wave propagates through an isotropic transparent medium through the various sample depths. Incidentally, this model assumption is also assumed in the prior art for the holoscopic volume reconstruction. Depending on the scattering strength of the sample, this model assumption is only applicable up to certain sample depths, depending on the employed spatial frequencies in the illumination and detection and the lateral resolution resulting therewith. By contrast, the assumption is no longer completely applicable at great measurement depths, and so the resolution in coherently reconstructed images is no longer better than in incoherently reconstructed images. In order to obtain an OCT recording with a very high penetration depth, as is necessary for retinal imaging on the eye (e.g., for the diagnosis of changes in the choroid), it is particularly preferable to limit the numerical aperture of the illumination wave, leading to the illumination speckle structures becoming coarser. Although, on the one hand, this reduces the maximum achievable lateral resolution, it simultaneously improves the suppression of the multiply scattered background at greater measurement depths. Technically, this can be achieved by virtue of, for example, the illumination wave being shadowed in a targeted manner by an (e.g., motor-driven) adjustable pupil stop. The provision (e.g., pivoting-in) of a diffusing plate in the intermediate image plane (e.g., a diffusing plate with smaller scattering angles) is a particularly preferred alternative. The scattering angles correspond to illumination apertures. "Smaller" means that the illumination apertures are smaller than the detection apertures.

The basic principles of the three variants can also be applied in line-scanning systems, with it being possible, in this case, to preferably make use of the known scan movement in order to displace the illumination speckle distribution over the retina in a targeted manner.

Typical OCT systems are preferably realized in "shot noise" limited fashion. As a result, the recording speed for a given sensitivity is only limited by the illumination intensity and the detection pupil size. The tissue of the iris and the retina have a similar sensitivity to thermal loads by the used illumination light sources. Therefore, the light limits for both eye portions (retina and anterior chamber) are similar according to the ophthalmological device standard DIN EN ISO 15004-2 and the laser standard DIN EN 60825-1 and lie of the order of 0.5 . . . 5 mW for a single-mode illumination. Even if the system is designed in such a way that the illumination focus lies in front of the eye, it is difficult to ensure from a technical point of view that, even in the case of eye movements and incorrect focusing, the illumination focus is never incident on the tissue of the eye, endangering the latter.

Significantly higher overall illumination intensities can be safely irradiated into the eye as a result of the multi-mode illumination since no relatively high peak intensities can occur in said eye as a result of the greater etendue. Thus, illumination waves with up to approximately 130 mW can be applied for line-scanning methods and a continuous power of up to 1 W can be applied for wide-field systems; this satisfies the relevant standards in both cases.

The light limits depend only on the illumination etendue and not on the coherence of the lightwave field. For this reason, the incoherent multi-mode illuminations can be realized with similarly high admissible illumination intensities. However, a coherent reconstruction outside of the focal plane is not possible in these systems as a result of the incoherence of the illumination.

For this reason, "time domain" systems are realized in such a way that the system is always actively focused onto the plane on which the delay is set. Hence, these systems require no coherent reconstruction. Partly coherent systems are also possible, in which, for example, detection is carried out with 1000×1000 pixels, but the illumination is only carried out by 100×100 modes. In these systems, the images can be coherently reconstructed locally (10×10 pixels wide). However, this also reduces the illumination etendue by a factor of 100 and hence significantly reduces the admissible illumination intensity.

However, the illumination etendue can be maximized on account of the coherent multi-mode illumination, without restrictions for coherent reconstruction. Hence, it is possible to realize significantly faster and more sensitive OCT measurements only by way of a coherent multi-mode illumination.

If the lateral resolution should be increased in a confocal system, it is possible in embodiments to adapt the illumination pupil imaging scale with a telescope and to illuminate and detect the retina with greater pupil diameters. Alternatively, it is also possible to only increase the illumination aperture/pupil diameter by way of the diffusing plate 100 in the illumination.

In a confocal system, the sensitivity outside of the focal plane decreases with $NA^4$ (NA=numerical aperture). The NA has to be doubled to double the lateral resolution.

For an unsymmetrical system with an illumination aperture that has been increased by the diffusing plate 100 and a detection with a smaller unchanged numerical aperture, the sensitivity outside of the focal plane only decreases with $NA^2$. However, the illumination aperture must be increased approximately 4-fold in order to double the resolution. Therefore, the sensitivity outside of the focal plane drops in a manner similar to a confocal system with a correspondingly higher NA.

The basic principle of the evaluation can be described as follows:

By way of example, the detector covers a pupil size of 0.65 mm. This corresponds to a focal size of approximately 35 µm on the retina 2 for a wavelength of approximately 1 µm. As a result of the diffusing plate 100, the illumination pupil is increased to 4.5 mm, for example. The diffusing element 100 is designed in such a way that the illuminated retinal region also has a diameter of approximately 35 µm. However, as a result of scattering of the wave, the 35 µm illumination spot is now modulated by approximately 37 speckle grains in its intensity. If two recordings of the retina 2 are now made, which are displaced in relation to one another by an illumination speckle grain, the two measured images are mathematically independent of one another as a result of the interaction with the retina 2. For this reason, the retina 2 is realized with greatly overlapping spots and, in the illustrated case of FIG. 1A, with a 5 µm scan advance between two OCT A-scans. As a result, a 3D image with a lateral sampling of 5 µm is obtained after the evaluation; however, this does not yet have the specified resolution as the object function is still convoluted with the illumination speckle pattern. If this speckle pattern is known for the focal plane, it can also be numerically propagated to all other planes via the waveguide equation. Hence, in the final image, there can be a coherent deconvolution of each 2D depth sectional image with the known speckle function. Here, in principle, all spatial frequencies up to the limit frequency are reconstructed, but some spatial frequencies are damped by the nature of the speckle. Since retinal images recorded in confocal fashion also have such a speckled structure, this is often acceptable from an application point of view.

In order to be able to coherently reconstruct the recordings, it is preferred for the absolute phase angle of the signals not to be falsified by movement artifacts for the recording of all overlaid retinal spots. This can be ensured for approximately 100 µs for typical movements of the retina. Thus, approximately ten individual measurements can be realized with a 100 kHz OCT system (A-scan rate) before this phase stability is no longer ensured. In the illustrated case, this means that the approximately seven overlapping spot images of a B-scan are phase-coupled to one another, but the OCT B-scans comprise statistical relative phase angles with respect to one another, and hence a coherent reconstruction is not possible. For this reason, the corresponding sample region of the retina, after an initial scan, will preferably be scanned once again with interchanged lateral directions (perpendicular scanning patterns) approximately every 5 . . . 10 A-scans in the design of FIG. 1A in order to locally estimate the phase angle relationships of the B-scans using these redundant information items and locally correct these before a coherent reconstruction.

For systems designed for the application on the living eye, the typical optical aberrations of the eye significantly restrict the achievable resolution for pupil diameters above approximately 1.3 mm. The prior art of holoscopy has disclosed that, and how, the eye aberrations can be estimated and removed from the data by calculation. The aberrations are iteratively estimated and corrected within the scope of the evaluation. Thus, not only a sharp image of the retina but also the wavefront aberrations of the measured eye are obtained in such systems.

If the intention is to use an OCT system as a wavefront sensor, the optimization target is to be able to measure the largest possible aberrations for a given pupil diameter. Since the method of coherent multi-mode illumination is unsymmetrical and only uses a large illumination aperture/pupil diameter, a significantly increased capture region for the aberration strength is obtained in comparison with a symmetrical confocal high-NA OCT system.

The prior art has disclosed a method referred to as multi-beam Doppler. Using this method, it is possible to quantitatively measure the speed and direction of flows such as, e.g., the blood flow in the capillaries of the retina using a plurality of confocal beams, which are simultaneously irradiated on a retinal point from different sub-pupils, but which are overlaid on the retina in temporally incoherent fashion. However, independently of the employed NA and on account of the system symmetry, it would not be possible to realize a quantitative 3D blood flow measurement using a single confocal sensor. However, on account of the coherent multi-mode illumination, it is now possible as a result of the speckle distribution in and around the focal spot to realize the latter in such a symmetry-free fashion that the 3D blood flow speed can be measured quantitatively in combination with a single confocal sensor.

According to the invention, the phase element 100 particularly preferably lies in the illumination beam path, conjugate to the retina 2. As a result, it is possible to pivot the diffusing plate 100 out of the beam path in motor-driven fashion and hence realize a confocal OCT, as corresponds to the prior art. Hence, the system can flexibly be switched between fast recordings, lateral high-resolution recordings or special recordings such as blood flow measurements or wavefront measurements.

In order to be able to measure an OCT image with a specified resolution, it is necessary to record and reconstruct all spatial frequencies that are less than or equal to a corresponding limit frequency. Therefore, there must be no gaps in the optical transfer functions because otherwise the spatial frequencies of the sample that fall in these gaps cannot be transferred by the system and then cannot be reconstructed either. The optical transfer function mathematically is the convolution of illumination pupil function and detection pupil function. If the intention is to completely suppress the described vignetting effect, the illumination pupil function and detection pupil function must be identical. If, additionally, there then should be no gaps in the transfer function, there must be no gaps in the detection pupil function. In systems that sequentially measure a plurality of sub-pupils and then coherently reconstruct these overall, the transfer function can be represented individually for each sub-pupil as a convolution of the illumination pupil function and the detection pupil function. Then, the overall transfer function is the sum of the individual transfer functions. If gaps in the detection pupil function occur in this type of vignetting-free assumption, it is not possible for spatial frequencies that fall in these gaps to be transferred by the system and these produce artifacts during the reconstruction. Consequently, the detection sub-pupil must completely fill the overall pupil in order to avoid reconstruction artifacts if there is no mode-crosstalk between the various illumination and detection modes.

The sub-pupils/detection channels must not exceed a certain diameter for a given eye pupil and an optical aberration level that is given by the application in order to prevent a "fringe washout" over the sub-pupils that is too strong. If, moreover, there must be no gaps in this detection pupil, the result of this is a minimum number of detectors that cannot be undershot for the purposes of obtaining a certain lateral resolution.

If a restricted vignetting effect is acceptable for the application, it is now possible to significantly reduce the necessary number of detector elements (19a.x/19b.x in FIG. 1B or pixels in FIG. 1C) in the detector device 17 if the gaps in the detection pupil function that surely arise as a result thereof are swamped by a gap-free illumination pupil function. As a result of the interactions of the various illumination modes with the various detection modes, the spatial frequencies of the illumination are transferred to the detection by the speckle modulation. For this reason, it is the idea to accept and/or optimize a certain vignetting effect in return for a reduced number of detector elements.

A pupil size of 4.5 mm (corresponds to a lateral resolution of 2.5 µm for $\lambda=1$ µm wavelength through large illumination and detection pupils) and a retinal field of approximately 60° should be captured with the lateral high-resolution OCT 1. Numerical solutions on an eye model can show that the size of the sub-apertures should not exceed 0.65 mm at the edge of the pupil in this case in order to restrict the "fringe washout" effect, which would limit the sensitivity. This yields a hexagonal arrangement with 37 detector elements of the detector device 17 as a minimal gap-free arrangement.

Thus, 37 directions would have to be scanned in succession using the known technique of multi-direction scanning OCT in order to achieve artifact-free imaging with the specified resolution. The outlay would be significantly higher.

Figure 4:
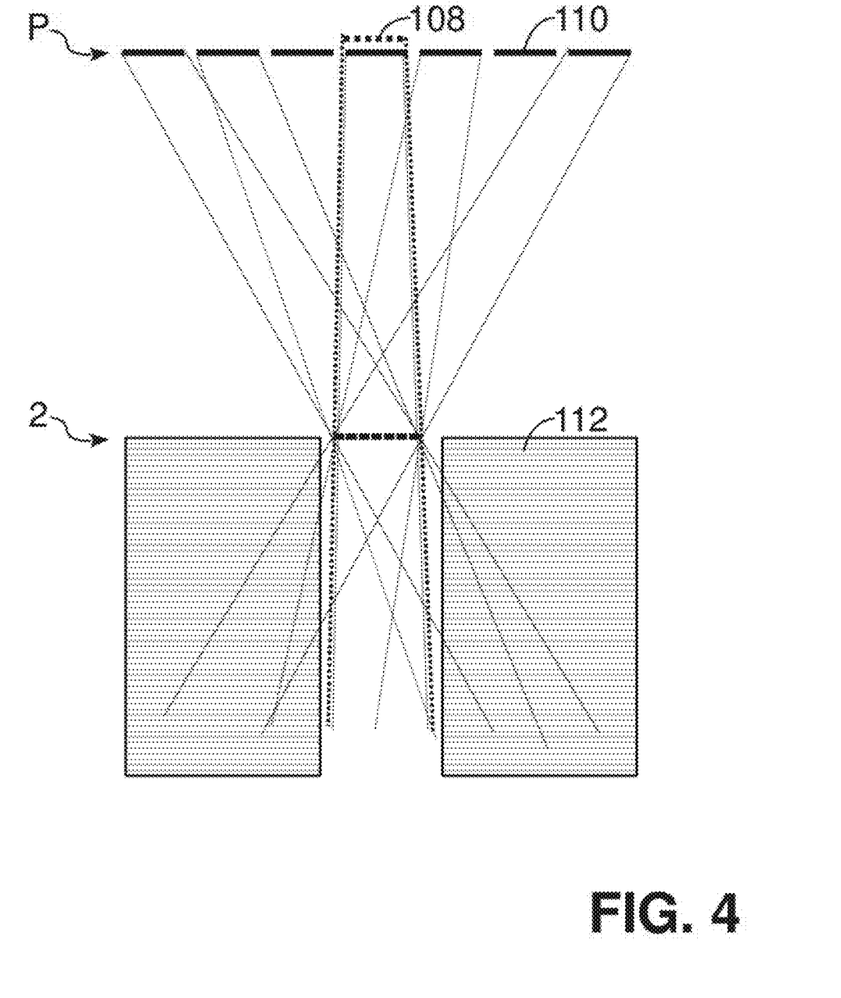
FIG. 4 shows a schematic illustration of an illumination vignetting effect, which may occur outside of the focal plane.
Figure 5:
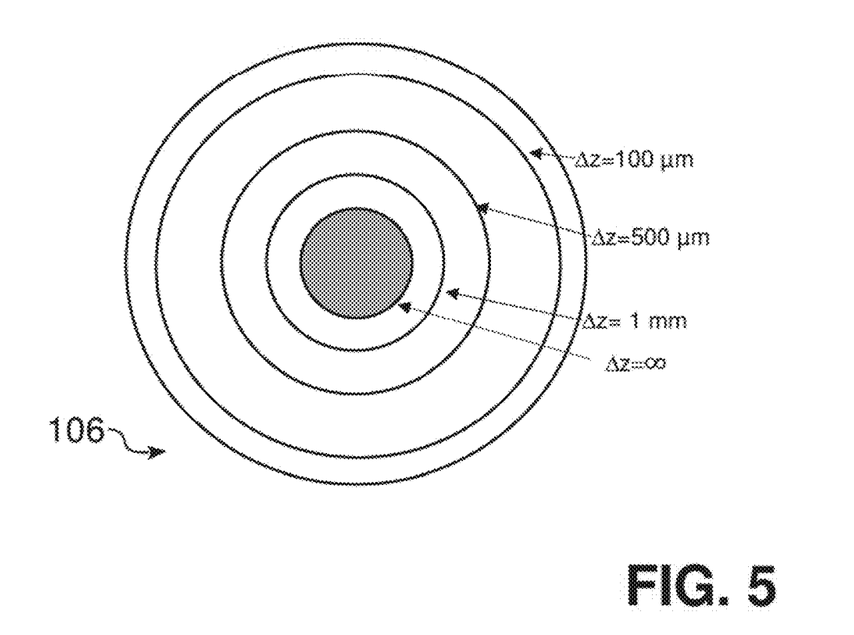
FIG. 5 shows regions of the sample which are not vignetted for a certain distance from the focal plane.

FIG. 4 schematically shows an illustration of the vignetting effect in the case of the so-called "mode mismatch" outside of the focal plane. FIG. 5 shows the relationships in the focal plane. The detector is situated at the location 108; the illumination is situated at the location 110. The hatched regions 112 are not used on account of vignetting effects since the illumination extends outside of the dashed region that can be captured of the location 108 of the detector. Here, for simpler explanation, locations 108 and 110 have been placed into the location of the pupil P; the vignetting is drawn below the retina 2. The regions 112 are illuminated but cannot be detected.

FIG. 5 shows the distance from the focus for which the vignetting just does not occur. In the central region, which corresponds to the dashed region in FIG. 4, there is no vignetting independently of the position in relation to the focal plane. Outside of the focal plane, the vignetting restricts the detectable numerical aperture, and hence the spatial frequency range accessible to the measurement, with increasing distance $\Delta z$.

Figure 7:
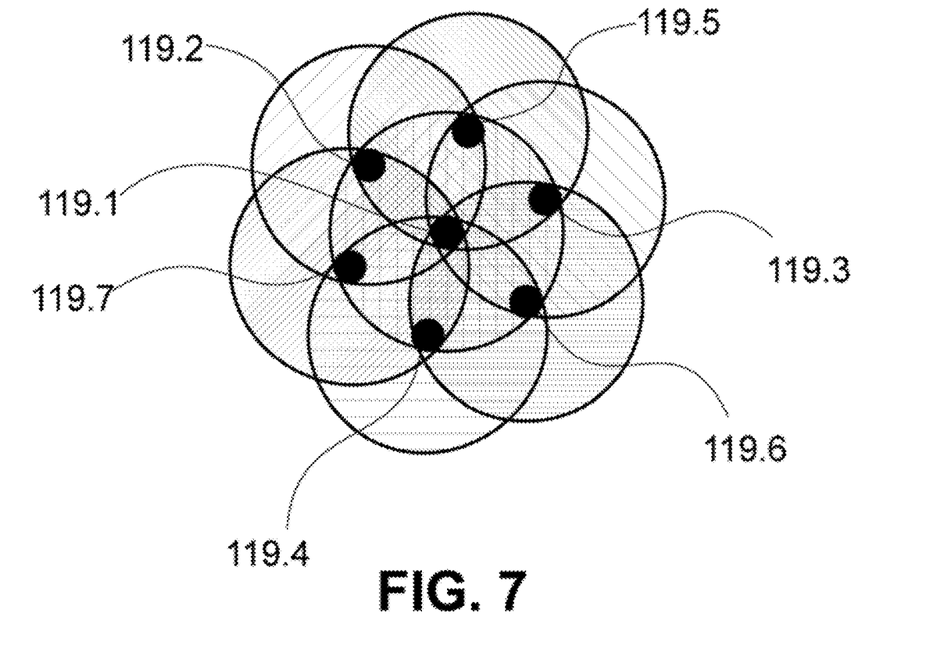
FIG. 7 shows an accessible spatial frequency spectrum for a 7-channel detection.

Only small retinal areas and only the uppermost retinal layers up to the RPE are measured in the case of retina imaging with such a high lateral resolution of 2.5 µm. For this reason, the depth range to be measured by the application can be restricted to, e.g., $\Delta z=500$ µm. If the area of the illumination in FIG. 7 is compared to the detector size, it is possible to identify that the detector device 17 can capture, even with vignetting effect, a spatial frequency range which uses, e.g., seven detectors (ring with six detectors around the central detector) for a vignetting-free system.

Figure 6:
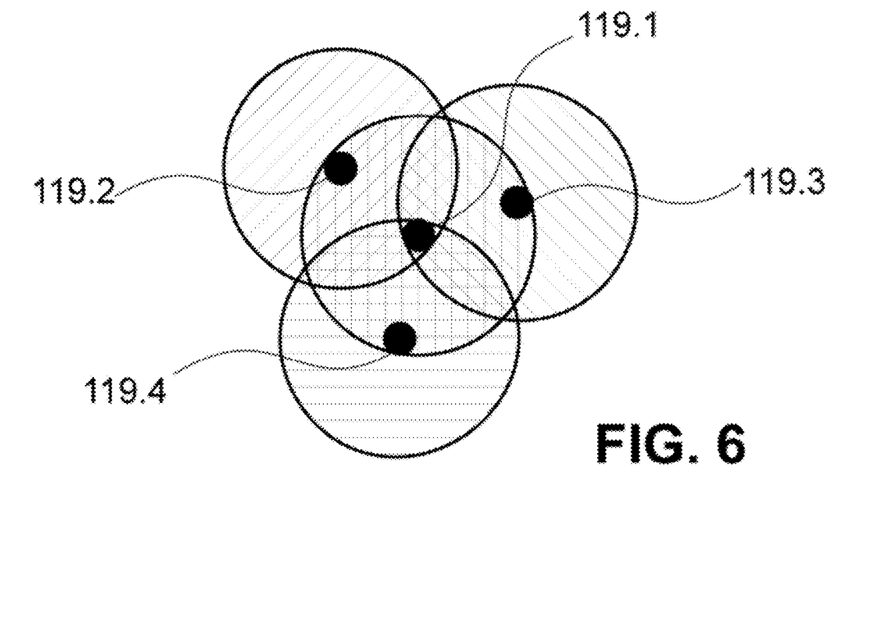
FIG. 6 shows an accessible spatial frequency spectrum for a 4-channel detection.

Multi-detector systems with a plurality (2 . . . 16) of sensor elements 19a.x/19b.x or pixels are therefore preferably combined with the coherent multi-mode illumination for the design of FIG. 1B or 1C. Various arrangements are conceivable to this end. The specific properties should be discussed in exemplary fashion below using two different arrangements, which are shown in FIGS. 6 and 7. FIG. 6 shows a system with a multi-detector system, which has four detector elements 119.1 to 119.4; FIG. 7 shows a variant with seven detector elements 119.1 to 119.7. Thus, the detector device 17 has four or seven detector elements, for example.

The central detector element 119.1 has three important objects in these arrangements. In the case of measurements on a living eye with a small usable iris diameter, the central location (e.g., pixel 119.1) ensures half the possible lateral resolution if the outer locations (pixels) are vignetted by the iris. The central location (pixel 119.1) significantly reduces the effect of vignetting outside of the focus for all measurements with a sufficient iris diameter. The data of the central position (detector 119.1) are redundant in the vicinity of the focus and can also be reconstructed independently from the other locations (detectors) with their overlapping spatial frequency spectra. Therefore, the data of the central location (pixel 119.1) can be used to reconstruct the absolute phase relationship between the B-scans in the case of overlapping scanning, without having to record additional perpendicular B-scans for the purposes of the local absolute phase correction.

The phase plate 100 should preferably also be arranged conjugatel to the retina 2 in the case of the detection with such multi-channel detection in order to be able to pivot-out the diffusing plate in motor-driven fashion or in order to be able to alternatively pivot-in different diffusing plates, which are optimized to certain applications.

The illumination shown in FIG. 4 with a filled pupil of an enlarged diameter is particularly suitable for a lateral high-resolution measurement without reconstruction artifacts as a result of gaps in the spatial frequency spectrum. The vignetting effect is significantly reduced in comparison with a confocal system that has been retrofitted with a diffusing plate 100 since the plurality of detectors 119.1-119.7 provide better coverage of the pupil. However, vignetting effects will still occur far outside of the focus.

By way of example, larger measurement depth ranges may be necessary if, for example, the intention is to measure the blood flow, important to the application, in the vessels of the choroid and the retina. In order to completely suppress the vignetting effect to this end, a phase plate 100 optimized to this end should be designed in such a way that it is not a filled diffusing pupil but respectively one illumination mode exactly at the associated detector position (with initial phase according to the main claim) that is produced.

Figure 8A:
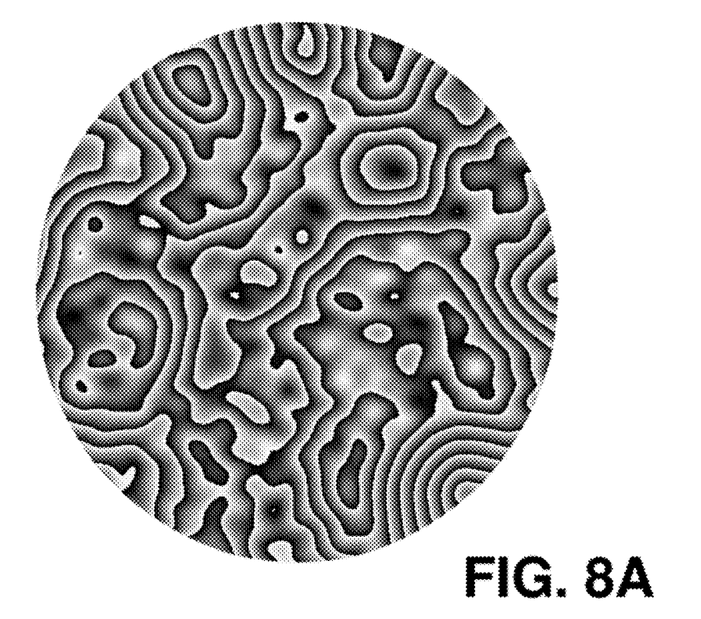
FIG. 8A shows a sectional magnification of a lithographically produced diffusing plate, which may be used in the microscope of FIG. 1A, 1B or 1C.
Figure 8B:
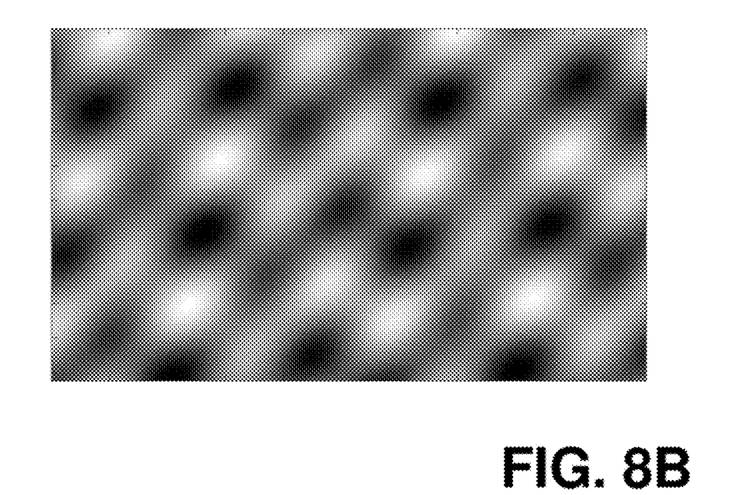
FIG. 8B shows a diffusing plate which produces one non-scattered and three scattered illumination modes.

It is shown in sectional fashion in FIG. 8A by way of example and produces a fully filled diffusing pupil and an unsymmetrical field distribution around the focal point. It is particularly suitable for high-resolution applications. Then, it may possibly be necessary to distribute the detector channels differently, e.g., as unsymmetrical as possible, in the detection pupil. FIG. 8B shows a diffusing plate which produces one non-scattered and three scattered illumination modes. The phase delays are encoded in gray in both images.

Naturally, it is also possible to use segmented detector arrangements, which completely fill the detection pupil, such as, e.g., a 37 pixel hexagonal detector array. From a technical point of view, systems with 2 to 100 separate detection channels can also particularly preferably be embodied as photonic integrated circuits.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method for holoscopic, optical coherence tomography for an object, in particular for an eye, wherein the method comprises:
   providing source radiation and splitting the source radiation into illumination radiation and reference radiation;
   illuminating an illumination field on the object with illumination radiation, said illumination field having an areal extent transverse to the direction of incidence;
   collecting illumination radiation scattered back from the object as measurement radiation;
   separating the measurement radiation collected from the object from the illumination radiation guided to the object; and overlaying the measurement radiation with reference radiation and detecting an interference signal of the overlaid radiations with at least one detector, wherein the object in the illumination field is simultaneously illuminated by more than one spatial radiation mode, wherein the radiation modes of the illumination in the illumination field are spatially and temporally coherent with one another but have a fixed phase difference from one another.

2. The method as claimed in claim 1, wherein the phase differences have a statistical or quasi-random distribution over the illumination field.

3. The method as claimed in claim 1, wherein confocal detection is carried out using the detector.

4. The method as claimed in claim 1, wherein the detector comprises a pair of balanced detectors.

5. The method as claimed in claim 1, wherein the detector comprises a detector with a spatial resolution in one dimension or two dimensions.

6. The method as claimed in claim 5, wherein the areal detector comprises detector elements lying next to one another in an image plane, wherein the number of detector elements and the number of illumination modes are matched to one another.

7. The method as claimed in claim 6, wherein the number of detector elements equals the number of illumination modes and the illumination modes are associated with the detector elements in bijective fashion.

8. The method as claimed in claim 5, wherein the number of detector elements is less than the number of illumination modes and information reconstruction is carried out from spatial frequencies, which are transferred by a mode interaction from the illumination to the detection.

9. The method as claimed in 1, wherein a plurality of individual recordings are made for the detector by detecting the interference signal of the overlaid radiations, the illuminations being displaced in relation to one another between said individual recordings by at least one illumination speckle grain, and wherein the individual recordings are combined to form an overall recording, preferably by averaging or by setting up and solving a system of equations by way of a linear regression.

10. The method as claimed in claim 1, wherein the object is illuminated in the illumination field using a speckle pattern that comprises no axis of symmetry.

11. An optical coherence tomography device for examining an object, in particular an eye, by means of holoscopy, said optical coherence tomography device comprising:
an illumination device for providing source radiation;
an illumination and measurement beam path, which comprises a splitting element for splitting the source radiation into illumination radiation and reference radiation, illuminates an illumination field on the object with the illumination radiation, said illumination field having an areal extent transverse to the direction of incidence, and collects illumination radiation scattered back from the object as measurement radiation; and
a detection beam path which receives the measurement radiation from the illumination and measurement beam path and the reference radiation from a reference beam path, and overlays said measurement radiation and reference radiation at an overlay site and guides these to a detector, wherein the illumination and measurement beam path illuminates the object in the illumination field simultaneously by more than one spatial radiation mode, and wherein the radiation modes of the illumination in the illumination field are spatially and temporally coherent with one another but have a fixed phase difference from one another.

12. The coherence tomography device as claimed in claim 11, wherein the detector comprises a confocal detector.

13. The coherence tomography device as claimed in claim 11, wherein the detector comprises an areal detector with a two-dimensional extent, said detector comprising 2 to 100 detector elements, in particular, and optionally being embodied as a photonic integrated circuit.

14. The coherence tomography device as claimed in claim 13, wherein the areal detector comprises detector elements lying next to one another in an image plane, wherein the number of detector elements and the number of illumination modes are matched to one another.

15. The coherence tomography device as claimed in claim 13, wherein the number of detector elements equals the number of illumination modes and the illumination modes are associated with the detector elements in bijective fashion.

16. The coherence tomography device as claimed in claim 13, wherein the number of detector elements is less than the number of illumination modes and the coherence tomography device comprises a control unit, which carries out an information reconstruction from spatial frequencies, which are transferred by a mode interaction from the illumination to the detection.

17. The coherence tomography device as claimed in claim 11, wherein the illumination and measurement beam path illuminates the object in the illumination field using a speckle pattern that comprises no axis of symmetry.

18. The coherence tomography device as claimed in claim 11, wherein the illumination and measurement beam path comprises a diffusing element for producing the illumination modes, said diffusing element being positioned in the illumination beam path, preferably in a field plane.

19. The coherence tomography device as claimed in claim 18, characterized in that the diffusing element is able to be pivoted out.

* * * * *

UNITED STATES PATENT AND TRADEMARK OFFICE
CERTIFICATE OF CORRECTION

| | | |
|---|---|---|
| PATENT NO. | : 11,064,879 B2 | Page 1 of 1 |
| APPLICATION NO. | : 16/440966 | |
| DATED | : July 20, 2021 | |
| INVENTOR(S) | : Daniel Bublitz | |

It is certified that error appears in the above-identified patent and that said Letters Patent is hereby corrected as shown below:

In the Claims

Column 19, Line 34, delete "1," and insert --claim 1,--

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*